US010110983B2

(12) United States Patent
Burgett et al.

(10) Patent No.: US 10,110,983 B2
(45) Date of Patent: Oct. 23, 2018

(54) EAR SIZING SYSTEM AND METHOD

(75) Inventors: Seth Burgett, Glen Carbon, IL (US); Richard J. Daniels, St. Louis, MO (US); David Fishbaine, Minnetonka, MN (US); Bharat Rajaram, Columbus, GA (US); Michael D. Wetle, St. Louis, MO (US); Tonya An, Grand Rapids, MI (US)

(73) Assignee: Harman International Industries, Incorporated, Stamford, CT (US)

( * ) Notice: Subject to any disclaimer, the term of this patent is extended or adjusted under 35 U.S.C. 154(b) by 576 days.

(21) Appl. No.: 13/399,058

(22) Filed: Feb. 17, 2012

(65) Prior Publication Data

US 2012/0242815 A1    Sep. 27, 2012

Related U.S. Application Data

(63) Continuation of application No. PCT/US2010/045773, filed on Aug. 17, 2010.

(60) Provisional application No. 61/234,405, filed on Aug. 17, 2009.

(51) Int. Cl.
| | |
|---|---|
| *H04N 7/18* | (2006.01) |
| *H04R 1/10* | (2006.01) |
| *A61B 5/107* | (2006.01) |
| *A61B 5/00* | (2006.01) |

(52) U.S. Cl.
CPC ......... *H04R 1/1016* (2013.01); *A61B 5/1079* (2013.01); *A61B 5/6815* (2013.01); *A61B 2576/02* (2013.01); *H04R 2201/105* (2013.01)

(58) Field of Classification Search
CPC ............ H04R 1/1016; H04R 2201/105; A61B 5/1079; A61B 5/6815; A61B 2576/02

USPC ............ 345/419; 348/77; 381/311, 17, 381; 703/13; 382/115; 73/37.9; 606/188

See application file for complete search history.

(56) References Cited

U.S. PATENT DOCUMENTS

| | | | |
|---|---|---|---|
| 5,592,248 A | 1/1997 | Norton et al. ............... 351/246 |
| 5,603,187 A | 2/1997 | Merrin et al. | |
| 6,053,931 A * | 4/2000 | Lizcano ....................... 606/188 |
| 6,692,127 B2 | 2/2004 | Abitbol et al. ............. 351/227 |
| 8,111,864 B2 * | 2/2012 | Oliveira et al. ............ 381/381 |
| 2003/0074174 A1 * | 4/2003 | Fu ..................... G05B 19/4099 |
| | | | 703/13 |
| 2004/0004633 A1 | 1/2004 | Perry et al. .................. 345/728 |
| 2004/0189935 A1 | 9/2004 | Warden et al. | |
| 2005/0082370 A1 | 4/2005 | Frantz et al. ........... 235/462.25 |

(Continued)

FOREIGN PATENT DOCUMENTS

| | | |
|---|---|---|
| CN | 2435706 Y | 6/2001 |
| CN | 201401994 Y | 2/2010 |
| DE | 20304099 U1 | 7/2003 |
| DE | 102005012054 A1 | 9/2006 |
| JP | 2002115374 A | 4/2002 |
| JP | 2003008046 A | 1/2003 |
| JP | 2003184235 A | 7/2003 |
| JP | 2005064147 A | 3/2005 |
| KR | 100915679 B1 | 9/2009 |
| WO | 9012990 A1 | 11/1990 |
| WO | 2009013607 A2 | 1/2009 |

(Continued)

OTHER PUBLICATIONS

European Supplemental Search Report, dated Sep. 23, 2013, pp. 5.

(Continued)

*Primary Examiner* — Joseph Suh
*Assistant Examiner* — Richard Carter
(74) *Attorney, Agent, or Firm* — Brooks Kushman, P.C.

(57) ABSTRACT

An ear measurement system and method include obtaining an image of an ear and an associated a calibration device, and analyzing the image to determine the size of desired portions of the ear. Such sizing is then used, for example, for fitting an earbud or earbud adapter.

20 Claims, 5 Drawing Sheets

(56) References Cited

U.S. PATENT DOCUMENTS

| | | | |
|---|---|---|---|
| 2005/0088435 A1* | 4/2005 | Geng | 345/419 |
| 2005/0238194 A1* | 10/2005 | Chornenky | H04R 1/1091 381/381 |
| 2006/0204013 A1 | 9/2006 | Hannibal et al. | 381/60 |
| 2007/0036376 A1* | 2/2007 | Fried | 381/312 |
| 2007/0036383 A1 | 2/2007 | Romero | |
| 2007/0183603 A1* | 8/2007 | Jin | A61B 5/1077 381/17 |
| 2008/0013794 A1* | 1/2008 | Kalker | G06K 9/00362 382/115 |
| 2009/0041287 A1* | 2/2009 | Quinlisk | 381/380 |
| 2009/0195678 A1 | 8/2009 | Zhao et al. | |
| 2010/0020221 A1 | 1/2010 | Tupman et al. | |
| 2011/0290005 A1* | 12/2011 | Hart | G01B 11/0658 73/37.9 |

FOREIGN PATENT DOCUMENTS

| | | | |
|---|---|---|---|
| WO | 2009120923 | A2 | 10/2009 |
| WO | 2011014655 | A2 | 2/2011 |

OTHER PUBLICATIONS

International Search Report, dated Oct. 7, 2010, p. 1.
PCT International Search Report, PCT/US2011/045773 (dated Jul. 3, 2012), 5 pages.

* cited by examiner

EAR SIZING SYSTEM AND METHOD

CROSS-REFERENCE TO RELATED APPLICATIONS

This Application is a continuation of PCT/US2010/045773, filed Aug. 17, 2010, which claims benefit of U.S. Provisional Application No. 61/234,405, filed Aug. 17, 2009, which are hereby incorporated by reference in their entirety.

BACKGROUND

Portable music players and portable telephones are becoming increasingly common. Owners of these and similar devices often prefer to use them in conjunction with personal sound delivery devices. These devices are worn, for example, while driving (e.g. telephone headset), exercising, traveling, or studying or the like.

Nearly all music players and portable phones have earbuds as a standard accessory, but these one-size-fits-all earbuds often do not stay in the user's ears or become uncomfortable over time.

Proper fitting earbuds or in custom ear monitors can provide the benefit of ambient noise isolation or suppression similarly to how earplugs block sound. However, stock earbuds often do not fit well enough to accomplish this.

In an attempt to address the above described earbud fit problems some companies offer kits of different size earbud adapters. The user selects, through a process of trial and error, the earbud adapter that fits his ear the best. While the probability of a better fit is thus increased, it is still inadequate because the variation in human ear anatomy is too great to be accommodated with a kit that is necessarily limited in its range of shapes and sizes. Furthermore, this approach requires the user to try on each earbud adapter and determine, sometimes over several hours use, if it provides the best fit. Finally, once the optimal earbud adapter is selected, the remaining ones are useless and this results in material waste. Some companies provide a single flexible or compliant earbud adapter where the user is able to adjust its shape and size and/or the material is able to be compressed and then expand to conform to the inner surfaces of the user's ear anatomy. This flexibility or compliance partially addresses the above mentioned problems with kits, but the extent of the flexibility or compliance is necessarily limited to provide optimal results for a small range of anatomy centered on the average ear. When purchasing this product, the user will typically not know in advance whether his ears will fall within the range of the adapter's accommodation which typically creates areas of pressure on known pain points within the ear.

To solve the above mentioned problems other companies supply full custom earbuds or earbud adapters. They do this by first injecting a soft material into the user's ear to form a physical impression or mould. The mould supplies the ear shape information that is then used to manufacture the custom fitted earbud or earbud adapter. While this full custom approach solves many of the problems outlined above, it requires a significant amount of skilled labor which elevates the production cost. Production costs are further increased because the full custom approach necessarily precludes mass production. Additionally, the user must undergo the moulding process which can be uncomfortable, scary and time consuming. And finally, the user must wait several business days while the custom solution is built and shipped. In this model, a custom fit earbud may require skilled labor to eliminate pressure points in areas known to be painful within the ear such as the Crus of Helix, the Tragus, the Anti-Tragus and the Anti-Helix.

For these and other reasons, there is a need for the present invention.

BRIEF DESCRIPTION OF THE DRAWINGS

FIG. 5 illustrates an image of an ear and calibration device overlayed with a template sizing tool.

DETAILED DESCRIPTION

Figure 1:
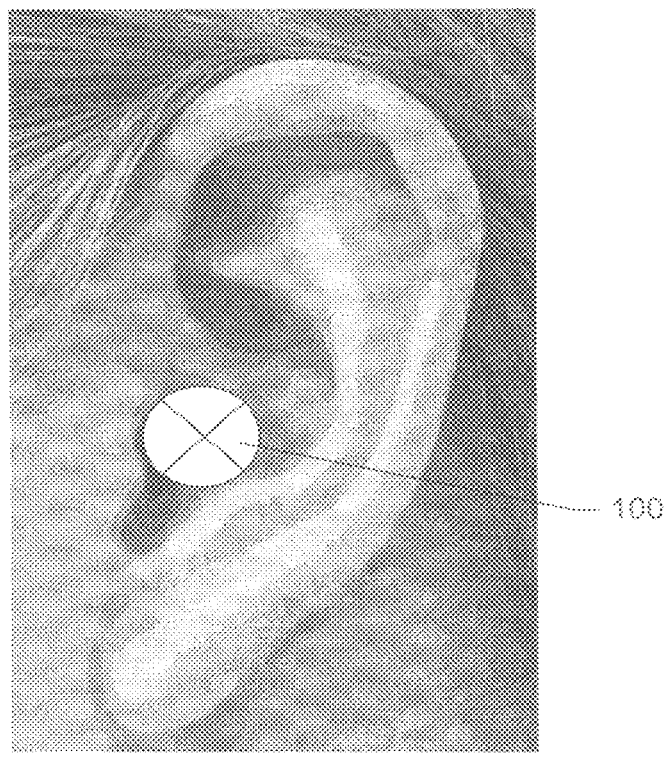
FIG. 1 illustrates an image of an ear and associated calibration device.

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

An earbud herein means a personal sound delivery device that fits substantially within the outer ear and which comprises an acoustic emitter.

An earbud adapter herein means a physical adapter that first, physically and acoustically connects to an earbud and second; physically and acoustically connects to the user's ear. An earbud adapter does not include an acoustic emitter.

An in ear monitor herein means a physical ear adapter that first, physically and acoustically contains an acoustic emitter and second; physically and acoustically connects to the user's ear through a contoured form to fit a single individuals ear. An in ear monitor contains an acoustic emitter that permanently or semi-permanently attaches an acoustic emitter and ear adapter.

An earpiece herein refers generically to devices such as an earbud, and earbud adapter or an in ear monitor.

Embodiments of systems and methods for sizing a user's ear for fitting an earpiece such as earbud adapters or earbuds are disclosed. In general, an ability to size the ear for earbud adapters or earbuds using a 2Dimensional image acquired from an image capture device such as common camera devices including mobile phones, hand held cameras, web cameras, etc. provides several advantages over existing systems and methods. Examples include 1. More accessible: The hand held camera can be used from any location, allowing web based ordering and rapid expansion of providing a custom sized earbud enhancer, with fulfillment systems that can be provided by mail or brick and mortar locations.

2. Lower cost: Three Dimensional (3D) imaging systems that are more expensive to 1-2 orders of magnitude are no longer required to fit individuals for custom sized earbud enhancers.

3. Safer: Some known 3D imaging systems for the ear use lasers or probes that can produce dangerous situations for the user or patient. Probes can create hazards including but not limited to abrasion or perforation. In some states, a licensed audiologist is required to produce an ear impression using a material injected into the ear and then extracted to produce an impression of the ear. This technique contains a risk of leaving material in the ear, perforation and other risks upon extraction.

4. Faster delivery: Once a user has taken the image, the image can be emailed, downloaded or processed on the imaging device (i.e. camera, camera phone etc) to communicate the correct size for the user. The user can then pickup the proper size at the retail location, order by phone or order by electronic communication to be preplaced at a retail location or mailed directly to the consumer.

5. Smaller size: Physics dictate that an angle of incidence required to achieve triangulation for 3D imaging systems is not required using a 2Dimensional imaging system. This means a smaller footprint, including handheld devices.

6. More robust: Many optical systems for 3D imaging do not provide for cameras that are impact resistant (drop from 1 meter or more). When compared to cameras currently available in mass production devices such as mobile phones or hand held cameras, 3D imaging systems are fragile and require special handling to prevent damage.

7. Higher tolerance: Lighting conditions for 3D imaging cameras may require reflective powder, special lighting or contain requirements to avoid fluorescent lighting. 2D imaging techniques do not require special lighting conditions that are different than requirements already placed on digital cameras.

Figure 2:
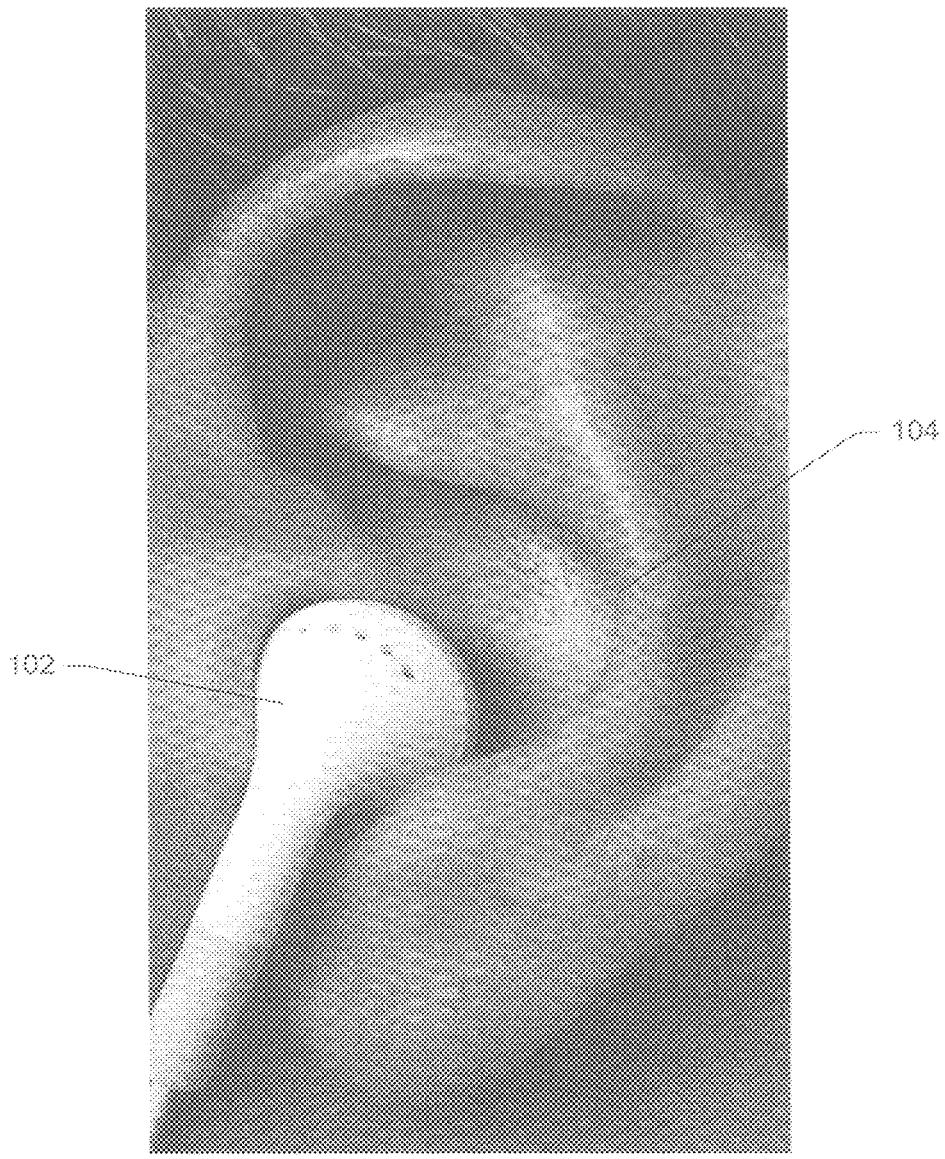
FIG. 2 illustrates an image of an ear including an earbud situated for use as a calibration device.
Figure 3:
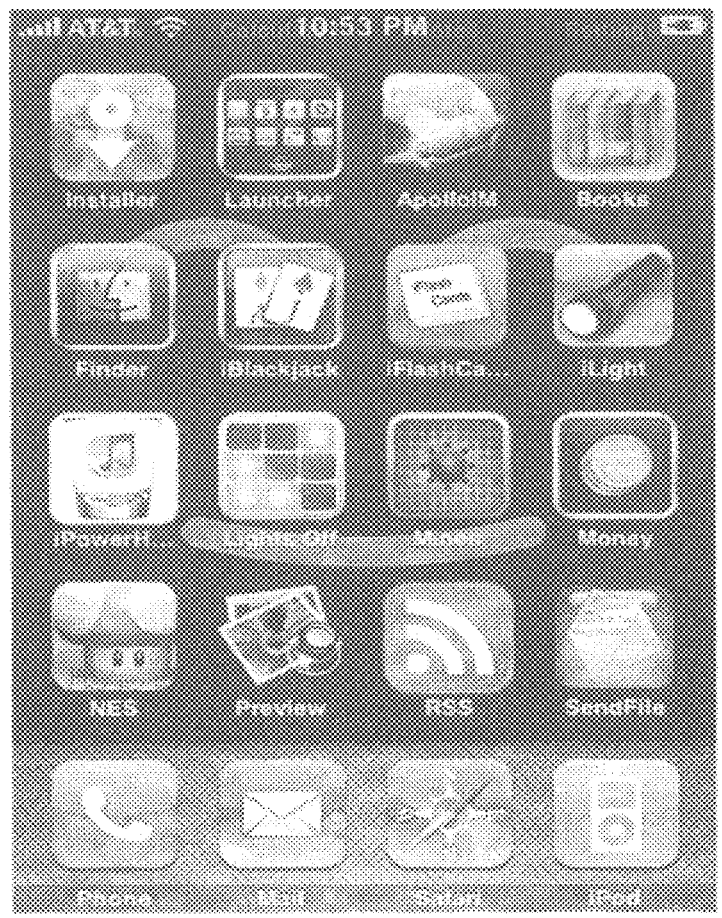
FIG. 3 illustrates an example of applications on a portable device such as a wireless phone.

In some disclosed embodiments, an image of the ear is taken using a digital camera device or a digitized photographic image or a video of an ear. In this manner, a dimension or multiple dimensions of the ear can be created that allows an ear prosthetic device such as an earbud adapter or earbud could be sized for the sample ear. During the image acquisition process, the size of the ear is calibrated to a known object such as a ruler, a gauge block, an earbud or any fixed device to calibrate the image such as is illustrated in FIG. 1, where a calibration device 100 is situated in the ear, and FIG. 2 where a known device such as an Apple earbud 102 is used for calibration. For example, various aspects of the earbud 102 in addition to the earbud itself can be used for calibration, including the diameter of the earbud, holes, arcs, diameter of the wire or wire connection, etc. The posterior edge 104 of the ear bowl, which is critical for determination of size, can be determined by comparing it to known dimensions of the earbud 102. The image acquisition can be provided by using an application on mobile phone, iPods, iTouchs, web cameras or digital cameras, such as illustrated in FIG. 3. Prior research and collection of data from an ear scan database of 3D ear images has shown that a 2D point-to-point measurement of an individual's ear is sufficient to assign size.

An application, such as an iPhone application as illustrated in FIG. 3, will facilitate the complete sizing and selling process using easy step-by-step instructions. First, a clear digital photo of the ear is captured. In some embodiments, only one ear is required for sizing, for instance, the left ear. As stated above, a reference object is included in the photo to minimize variability in the scale of the image as illustrated in FIGS. 1 and 2. The image of the ear could be taken by a second individual, although embodiments are envisioned where clear instructions describe the approximate angle and distance for self-photographing. The application will show all procedural steps accompanied by illustrations and image examples of "acceptable" vs. "incomplete" ear photos. When satisfied with the image, the consumer electronically sends the image for manual sizing. Input of personal information (Name, email, phone number) may be required prior to this point and will also be integrated into the application software.

Figure 4:
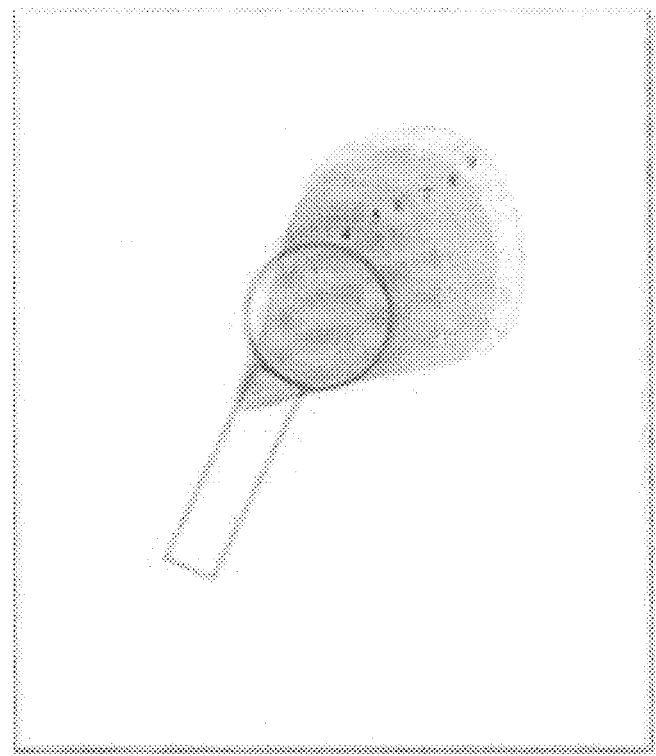
FIGS. 4 and 5 illustrates a template sizing tool
Figure 5:
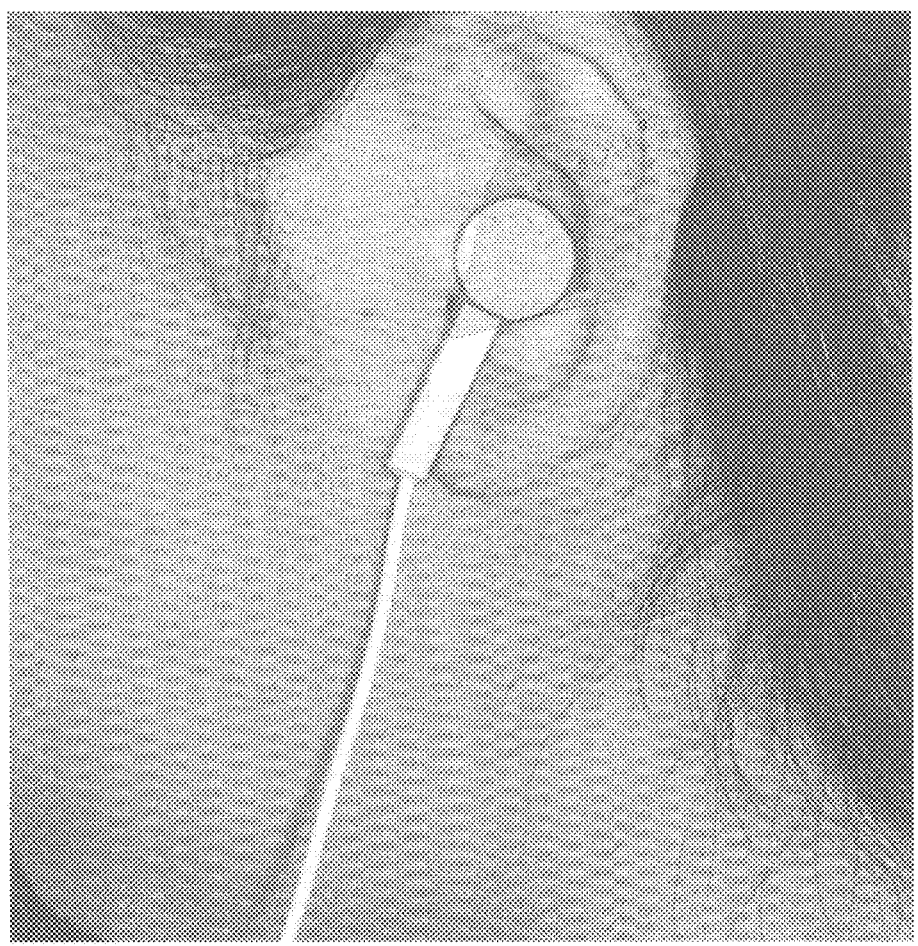

New or existing software can be applied toward photo manipulation and sizing. Upon receipt of the file containing the image, it is manually or automatically uploaded into a sizing program. For proper sizing, the dimensions of the reference object are calibrated to determine the scale of the image. In certain embodiments, this is done manually by opening the image in a photo-editing program, i.e. Adobe Photoshop. A predesigned template sizing tool is scaled to match the size of the reference earbud or other calibration device included in the image with the user's ear. Overlaying the template tool on the ear image allows for visual comparison of the edge of the bowl on an individual's ear to earbud size outlines (see FIGS. 4 and 5) and assignment of closest earbud enhancer size. Algorithms may be designed to minimize variability in sizing. The sizing process can be completed quickly by a staff person. Immediately following, a message containing the custom size and order information can be sent via email or directly through the application interface to the iPhone or similar device. Ideally, the process should not take more than five minutes between the consumer taking and sending the picture to receiving her size. Account and ordering information must be integrated into the app, as well as FAQ, support and help functions.

The automated model requires object recognition software that recognizes the white earphone bud and automatically scale the template to size. It also requires edge recognition to determine the best correlation between the posterior bowl edge and the size outlines. Output from this process will correspond to the emailing of the specific size back to the individual with minimal turnover time.

The iPhone app will serve multiple purposes such as brand promotion, market targeting, order collection and processing in addition to the primary sizing function. The sizing component of the software will be constant, but the platform can be adapted to any mobile phone with camera capabilities and SMS or MMS. Website sizing can also be achieved by upload of any digital photo or flash-enabled use of webcam capture. Sizing results can be returned via email or website account.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An ear measurement method, comprising:
   obtaining a two-dimensional image including both at least a portion of an ear and an associated calibration device, said associated calibration device being a reference object;

comparing the associated calibration device to a predesigned template;
determining a sizing parameter based on a difference in size between the image of the calibration device and the predesigned template; and
determining an ear size by applying the sizing parameter to the image of the ear.

2. The method of claim 1, wherein obtaining the two-dimensional image of the ear and the associated calibration device further comprising capturing the two-dimensional image via mobile device.

3. The method of claim 1, further comprising sizing an earpiece based on the ear size.

4. The method of claim 3, further comprising delivering the earpiece to a consumer.

5. The method of claim 1, further comprising transmitting the two-dimensional image of the ear and the associated calibration device over a network to be analyzed.

6. An earpiece sizing system, comprising:
an image capture device;
a sizing program configured to receive a two-dimensional image of both an ear and a calibration device from the image capture device, comparing the image of the calibration device to a predesigned template, determine a sizing parameter based on a difference in size between the image of the calibration device and the predesigned template, and determining a size of the ear within the two-dimensional image by applying the sizing parameter to the ear within the two-dimensional image for sizing an earpiece.

7. The system of claim 6, wherein the image capture device is a camera.

8. The system of claim 6, wherein the image capture device includes a mobile phone.

9. The system of claim 6, wherein the calibration device is an earbud.

10. The system of claim 9, wherein the sizing parameter is determined based on a difference in a known diameter of the earbud with a diameter of the earbud within the image.

11. The system of claim 6, wherein the calibration device is a ruler.

12. The system of claim 6, wherein the calibration device is a gauge block.

13. The system of claim 6, wherein the two-dimensional image includes a posterior edge of the ear and wherein the sizing program is further configured to determine a size of the posterior edge based on the at least on the sizing parameter.

14. The system of claim 6, wherein the sizing parameter is determined based on a difference in a known dimension of a calibration device and a dimension of the image of the calibration device.

15. A method of selecting an appropriate size earpiece selecting method, comprising:
obtaining a two-dimensional image including both an ear and an associated calibration device, the associated calibration device being a known reference object;
comparing the image of the calibration device to a scaling template;
determining a sizing parameter based on a difference in size between the image of the calibration device and the scaling template;
determining an ear size based on the sizing parameter; and
assigning an earpiece based on the ear size.

16. The method of claim 15, wherein obtaining the two-dimensional image of the ear and the associated calibration device further comprising capturing the two-dimensional image via a mobile device.

17. The method of claim 15, wherein the two-dimensional image of the ear and the associated calibration device is received from a mobile device.

18. The method of claim 15, wherein assigning the earpiece includes selecting an earpiece corresponding to the ear size.

19. The method of claim 15, further comprising delivering the earpiece to a consumer.

20. The method of claim 15, further comprising transmitting the two-dimensional image of the ear and the associated calibration device over a network to be analyzed.

* * * * *